US012733818B2

(12) United States Patent
Kim

(10) Patent No.: US 12,733,818 B2
(45) Date of Patent: Sep. 15, 2026

(54) DISPOSABLE ELECTRONIC THERMOMETER

(71) Applicant: AMOSENSE CO., LTD, Cheonan-si (KR)

(72) Inventor: Beom Jin Kim, Cheonan-si (KR)

(73) Assignee: AMOSENSE CO., LTD, Cheonan-si (KR)

( * ) Notice: Subject to any disclaimer, the term of this patent is extended or adjusted under 35 U.S.C. 154(b) by 865 days.

(21) Appl. No.: 18/002,829

(22) PCT Filed: Jun. 10, 2021

(86) PCT No.: PCT/KR2021/007275

§ 371 (c)(1),
(2) Date: Dec. 21, 2022

(87) PCT Pub. No.: WO2022/005041

PCT Pub. Date: Jan. 6, 2022

(65) Prior Publication Data

US 2023/0240540 A1 Aug. 3, 2023

(30) Foreign Application Priority Data

Jun. 29, 2020 (KR) ........................ 10-2020-0079245

(51) Int. Cl.
*A61B 5/00* (2006.01)
*A61B 5/01* (2006.01)
(Continued)

(52) U.S. Cl.
CPC ................ *A61B 5/01* (2013.01); *A61B 5/002* (2013.01); *G01K 13/20* (2021.01); *H01Q 7/00* (2013.01);
(Continued)

(58) Field of Classification Search
CPC ... A61B 5/01; A61B 5/002; A61B 2560/0219; A61B 2560/0285; A61B 2562/0271;
(Continued)

(56) References Cited

U.S. PATENT DOCUMENTS 10,390,759 B2 * 8/2019 Quinn .................... A61B 5/002
10,993,657 B1 * 5/2021 Miller .................... G01N 25/62
(Continued)

FOREIGN PATENT DOCUMENTS

IT 201800005112 A1 * 11/2019 ........... A61B 5/6833
JP 2017-181411 A 10/2017
(Continued)

OTHER PUBLICATIONS

International Search Report for PCT/KR2021/007275 by Korean Intellectual Property Office dated Sep. 27, 2021.
(Continued)

*Primary Examiner* — May A Abouelela
(74) *Attorney, Agent, or Firm* — BROADVIEW IP LAW, PC

(57) ABSTRACT

A disposable electronic thermometer is provided. The disposable electronic thermometer, according to an exemplary embodiment of the present invention, comprises: a base substrate including an adhesive layer formed on one surface to be attached to a body of a user; a control part including a circuit board arranged on one surface of the base substrate and at least one driving chip mounted on the circuit board; a temperature sensor arranged on one surface of the base substrate and electrically connected to the circuit board, to thus measure a body temperature of a user; an NFC antenna electrically connected to the circuit board and arranged on one surface of the base substrate to surround the circuit board; and a cover member attached to one surface of the
(Continued)

base substrate to prevent external exposure of the circuit board, the temperature sensor, and the NFC antenna.

8 Claims, 5 Drawing Sheets

(51) Int. Cl.
*G01K 13/20* (2021.01)
*H01Q 7/00* (2006.01)

(52) U.S. Cl.
CPC ................ *A61B 2560/0219* (2013.01); *A61B 2560/0285* (2013.01); *A61B 2562/0271* (2013.01)

(58) Field of Classification Search
CPC ... A61B 5/0008; A61B 5/6833; A61B 5/0015; A61B 2562/166; G01K 13/20; G01K 1/024; G01K 1/08; G01K 13/25; H01Q 7/00; H01Q 1/273; H01Q 1/2225
See application file for complete search history.

(56) References Cited

U.S. PATENT DOCUMENTS 11,173,341 B2* 11/2021 Kim ................... A63B 24/0062
11,701,250 B2* 7/2023 Smith .................... G01K 1/143 62/3.5
11,872,018 B2* 1/2024 Abreu .................. A61B 5/7425
12,171,570 B2* 12/2024 Pieri ...................... A61B 5/273
2005/0226310 A1* 10/2005 Nakazawa ............. G01K 1/024 374/E1.004
2006/0122473 A1* 6/2006 Kill ........................... G01J 5/08 374/E1.004
2007/0055171 A1* 3/2007 Fraden ................... G01K 1/165 374/E7.042
2014/0088443 A1* 3/2014 Van Den Heuvel ........................ A61B 5/7282 600/483
2014/0121557 A1* 5/2014 Gannon ................. G01K 1/024 600/549
2014/0206976 A1* 7/2014 Thompson ............... A61B 5/25 600/391
2014/0266939 A1* 9/2014 Baringer .................. H01Q 1/22 343/729
2015/0148681 A1* 5/2015 Abreu .................. A61B 5/6821 600/474
2015/0173674 A1* 6/2015 Hayes .................... G16H 40/67 600/300
2015/0335254 A1* 11/2015 Fastert ................. A61B 5/7275 600/549
2015/0351690 A1* 12/2015 Toth ................... A61B 5/14542 600/391
2016/0249174 A1* 8/2016 Patel ........................ A61B 5/01
2016/0310049 A1* 10/2016 Rowe ..................... A61B 5/681
2017/0209055 A1* 7/2017 Pantelopoulos ..... A61B 5/7203
2017/0245797 A1* 8/2017 Quinn .................. A61B 5/6833
2017/0248475 A1* 8/2017 Bonifas .................. G01N 25/18
2017/0281022 A1* 10/2017 Nakashima .......... A61B 5/6801
2018/0028071 A1* 2/2018 Shi ......................... A61B 5/282
2018/0028072 A1* 2/2018 Shi ....................... A61B 5/6833
2018/0160952 A1* 6/2018 Hsieh .................. A61B 5/6823
2018/0184902 A1* 7/2018 Meyerson ................ A61B 5/01
2019/0046033 A1* 2/2019 Gannon ................. G01K 1/024
2019/0082968 A1* 3/2019 Karnik ..................... A61B 5/01
2019/0132948 A1* 5/2019 Longinotti-Buitoni ...................... A61B 5/6805
2019/0133088 A1* 5/2019 Hurley ..................... A61B 5/11
2019/0213461 A1* 7/2019 Kato ................ G06K 19/07777
2019/0328327 A1* 10/2019 Kim ......................... H04B 5/79
2019/0343397 A1* 11/2019 Meisal ..................... A61B 5/01
2019/0365263 A1* 12/2019 Raj ...................... A61B 5/0024
2020/0037949 A1* 2/2020 Subbhuraam ........ A61B 5/7275
2020/0069190 A1* 3/2020 Ryu ......................... H01Q 7/00
2020/0129112 A1* 4/2020 Model .................... G16H 20/00
2020/0309608 A1* 10/2020 Shimuta ................... G01K 7/16
2020/0335211 A1* 10/2020 Gopalakrishnan ........ G06F 8/61
2020/0405228 A1* 12/2020 Svanegaard .......... A61F 5/4404
2021/0000351 A1* 1/2021 Murali ..................... A61B 5/25
2021/0077304 A1* 3/2021 Xu ........................... H04B 5/26
2021/0204819 A1* 7/2021 Kim ....................... G16H 50/20
2021/0267462 A1* 9/2021 Kim ....................... A61B 5/002
2021/0345878 A1* 11/2021 Khalil .................. A61B 5/6802
2021/0353219 A1* 11/2021 Narayanan ........... A61B 5/4809
2021/0369125 A1* 12/2021 Medeiros ............. A61B 5/0022
2022/0000375 A1* 1/2022 Meisal ..................... A61B 5/28
2022/0079438 A1* 3/2022 Baek .................... A61B 5/6833
2022/0257429 A1* 8/2022 Akrami ................ A61B 5/0022
2022/0304622 A1* 9/2022 Freckleton ............ G16H 40/63

FOREIGN PATENT DOCUMENTS

KR 10-2015-0066560 A 6/2015
KR 10-2015-0083321 A 7/2015
KR 10-2016-0015419 A 2/2016
KR 20170010662 A * 2/2017 ............... A61B 5/01
KR 20170017560 A * 2/2017 ............... A61B 5/01
KR 10-2018-0092473 A 8/2018
KR 20190033753 A * 4/2019 ............. G06Q 50/22
KR 10-2020-0021711 A 3/2020
WO WO-2014125726 A1 * 8/2014 ............. G01K 13/20
WO WO-2018209100 A1 * 11/2018 ............. A61B 5/445
WO WO-2019054776 A1 * 3/2019 ............... A61B 5/01
WO WO-2020206372 A1 * 10/2020 ............... H04B 5/45

OTHER PUBLICATIONS

Office Action for KR 10-2020-0079245 by Korean Intellectual Property Office dated Nov. 18, 2025.

* cited by examiner

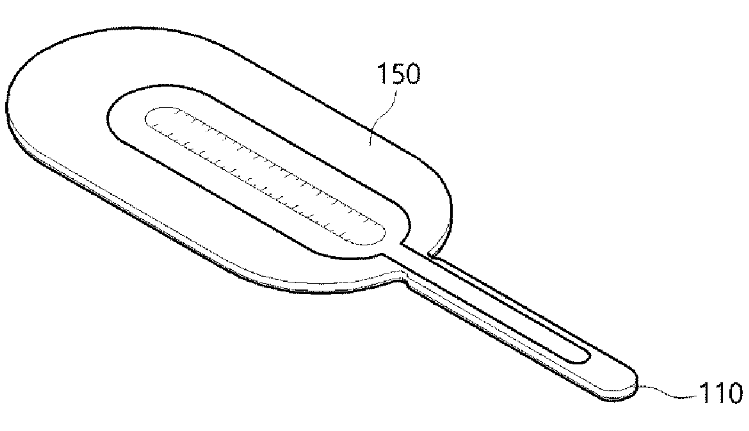
FIG. 1
100, 200
110
150
113
160
FIG. 2

DISPOSABLE ELECTRONIC THERMOMETER

CROSS-REFERENCE TO RELATED APPLICATIONS

This application is a National Phase Entry Application of PCT Application No. PCT/KR2021/007275 filed on Jun. 10, 2021, which claims priority to Korean Patent Application No. 10-2020-0079245 filed on Jun. 29, 2020, in Korean Intellectual Property Office, the entire contents of which are hereby incorporated by reference in its entirety.

TECHNICAL FIELD

The present invention relates to a disposable electronic thermometer.

BACKGROUND ART

Recently, infectious diseases such as corona virus are spreading all over the world. Among the early symptoms of such infectious diseases, a typical symptom is fever.

Accordingly, in order to quickly determine whether an infectious disease accompanied by fever is infected, it is necessary to continuously monitor changes in body temperature.

Moreover, since the infectious diseases such as corona virus have an incubation period of about two weeks, it is necessary to continuously check body temperature changes for a certain period of time even if no special symptoms appear.

However, when the body temperature is measured with a general thermometer, it is cumbersome to measure the body temperature because the thermometer must be kept in contact with a body part such as an armpit or an ear for a certain period of time.

In particular, when a user continuously needs to perform a dynamic task, the conventional thermometer has difficulty in continuously measuring the body temperature.

DISCLOSURE

Technical Problem

The present invention is directed to providing a disposable electronic thermometer capable of easily measuring a user's body temperature while being attached to the user's body and being removed from the body after use.

Technical Solution

One aspect of the present invention provides a disposable electronic thermometer comprising: a base substrate including an adhesive layer formed on one surface so as to be attached to a user's body; a control part including a circuit board disposed on one surface of the base substrate and at least one driving chip mounted on the circuit board; a temperature sensor disposed on one surface of the base substrate and electrically connected to the circuit board to measure the user's body temperature; an NFC antenna disposed on one surface of the base substrate to surround the circuit board while being electrically connected to the circuit board; and a cover member attached to one surface of the base substrate to prevent external exposure of the circuit board, the temperature sensor and the NFC antenna.

In addition, the base substrate may be a porous substrate. For example, the base substrate may be made of a material without toxicity and skin irritation, and may be a woven fabric, a knitted fabric, a nonwoven fabric, a membrane, or the like.

Further, the base substrate may include a plate-shaped first portion in which the circuit board and the NFC antenna are disposed on one surface thereof, and a second portion extending a certain length from the first portion to have a smaller area than the first portion and where the temperature sensor is disposed. In this case, the circuit board may be provided to have an area corresponding to a partial area of the total area of the first portion. As a non-limiting example, the total area of the circuit board may be an area corresponding to a partial area of the total area corresponding to the inner region of the NFC antenna.

In addition, the temperature sensor may be electrically connected to the circuit board through at least one wire having one end connected to the circuit board, and the NFC antenna may be a coil in which a wire having a predetermined length is wound multiple times. In this case, the coil may be disposed on one surface of the base substrate to surround an edge of the circuit board from the outside of the circuit board.

In addition, the cover member may be a plate-shaped film member.

Meanwhile, the disposable electronic thermometer according to one embodiment of the present invention may have a built-in driving power source or may receive driving power from the outside in an energy harvesting method.

For example, the disposable electronic thermometer may receive driving power through the NFC antenna when NFC tagging is performed.

In this case, the control part may further include a memory part for storing body temperature information measured by the temperature sensor, and may transmit the body temperature information measured by the temperature sensor to the outside through the NFC antenna.

As another example, the disposable electronic thermometer may further include a power supply part for providing driving power to the control part.

In this case, the control part may further include a memory part for storing body temperature information measured by the temperature sensor, and may measure the user's body temperature at regular time intervals through the temperature sensor and store the measured information in the memory part, and the information stored in the memory part may be transmitted to the outside through the NFC antenna when NFC tagging is performed.

Advantageous Effects

According to the present invention, the electronic thermometer can easily measure a user's body temperature while being attached to the user's body, and can be removed from the body after use, thereby increasing convenience of use.

In addition, according to the present invention, the user's body temperature change can be tracked through the body temperature information stored in the memory part, whereby the user's fever can be easily monitored.

DESCRIPTION OF DRAWINGS

FIG. 1 is a view showing a disposable electronic thermometer according to the present invention.

FIG. 2 is a bottom view showing a state in which a release film is separated in FIG. 1.

MODE FOR INVENTION

Figure 3:
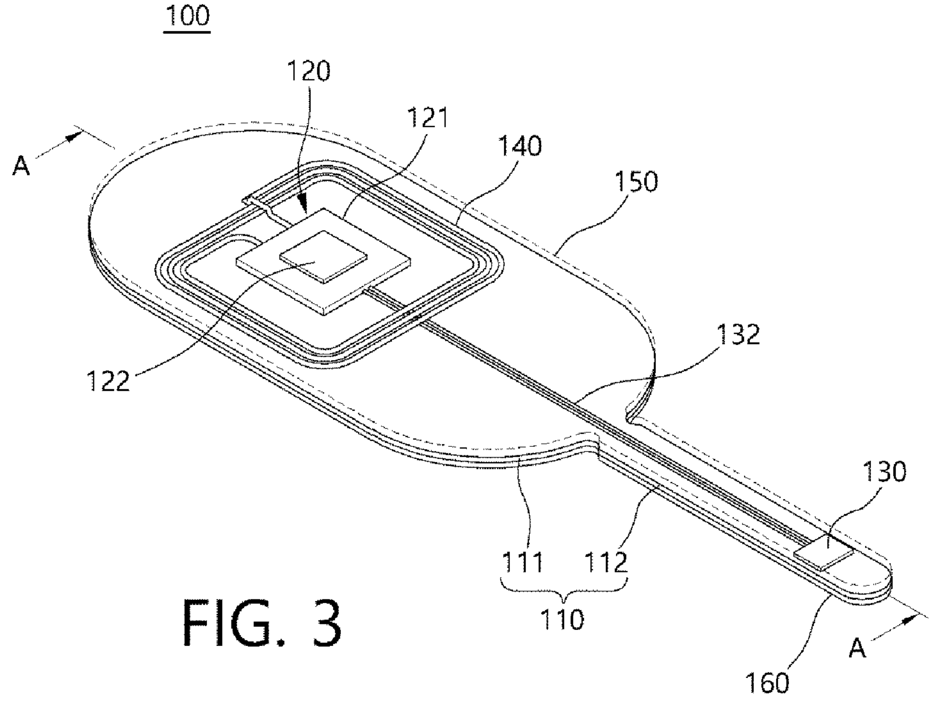
FIG. 3 is a view showing an internal configuration of a disposable electronic thermometer according to one embodiment of the present invention.

Hereinafter, with reference to the accompanying drawings, embodiments of the present invention will be described in detail so as to be easily implemented by one of ordinary skill in the art to which the present invention pertains. The present invention may be embodied in a variety of forms and is not be limited to the embodiments described herein. In order to clearly describe the present invention in the drawing, parts irrelevant to the description are omitted from the drawings; and throughout the specification, same or similar components are referred to as like reference numerals.

A disposable electronic thermometer 100 or 200 according to one embodiment of the present invention is implemented in the form of a patch so that it may be easily attached to a user's body, and may easily measure the user's body temperature while being attached to the user's body.

In addition, the disposable electronic thermometer 100 or 200 according to one embodiment of the present invention may be easily removed from the user's body in a case in which there is no need to measure the body temperature, thereby increasing convenience of use.

To this end, the disposable electronic thermometer 100 or 200 according to one embodiment of the present invention includes a base substrate 110, a control part 120, a temperature sensor 130, an NFC antenna 140 and a cover member 150 as shown in FIGS. 1 to 6.

The base substrate 110 may be formed in a plate shape having a predetermined area. One surface of the base substrate 110 may support the control part 120, the temperature sensor 130 and the NFC antenna 140, and the other surface may provide an attachment surface that is attached to the user's body.

For example, an adhesive layer 113 may be formed on a lower surface of the base substrate 110 so as to be attached to the user's body, and the control part 120, the temperature sensor 130 and the NFC antenna 140 may be disposed on an upper surface of both surfaces of the base substrate 110, which is opposite to the surface on which the adhesive layer 113 is formed.

Here, the adhesive layer 113 may provide adhesion or stickiness, and may be a gel-type adhesive or a known double-sided tape.

In this case, a release film 160, which is removed when used, may be attached to the exposed surface of the adhesive layer 113.

Accordingly, the user may expose the adhesive layer 113 to the outside by removing the release film 160 from the disposable electronic thermometer 100 or 200, whereby the disposable electronic thermometer 100 or 200 may be easily attached to a body part through the adhesive layer 113 exposed to the outside. In addition, when there is no need to measure the user's body temperature, the user may easily remove the disposable electronic thermometer 100 or 200 attached to the body.

Such a base substrate 110 may be made of a material having no toxicity and skin irritation, and may be made of a flexible material so that it may be smoothly and closely attached to the user's skin. In addition, the base substrate 110 may be formed of a porous material to ensure permeability.

For example, the base substrate 110 may be formed of a woven fabric, a knitted fabric, a non-woven fabric, a membrane, etc. to ensure breathability and flexibility.

However, the material of the base substrate 110 is not limited thereto, and any material that has flexibility and is harmless to the human body may be used without limitation. As a non-limiting example, the base substrate 110 may be formed of a soft synthetic resin film such as polyvinyl chloride (PVC) or polyurethane. Further, in addition to the above-described material, any known material used as a medical band may be used for the base substrate 110.

The control part 120 may control the overall operation of the disposable electronic thermometer 100 or 200 according to one embodiment of the present invention, and may be disposed on one surface of the base substrate 110 as described above.

To this end, the control part 120 may include a circuit board 121 disposed on one surface of the base substrate 110 and at least one driving chip 122 mounted on the circuit board 121.

As a non-limiting example, the driving chip 122 may be a system semiconductor such as an MCU, and may control driving of the NFC antenna 140.

Figure 7:
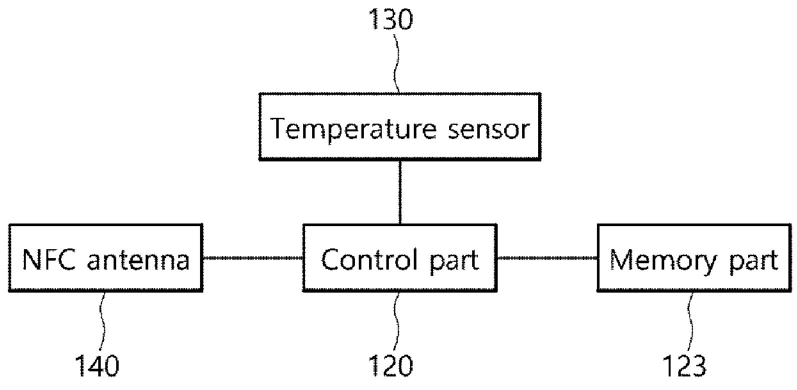
FIG. 7 is a block diagram showing a configuration of a disposable electronic thermometer according to one embodiment of the present invention.

In addition, the control part 120 may further include a memory part 123 (see FIG. 7) capable of storing body temperature information measured by the temperature sensor 130.

In this case, the disposable electronic thermometer 100 or 200 according to one embodiment of the present invention may reduce the production cost by minimizing the amount of the circuit board 121 used.

That is, in the present invention, the circuit board 121 may have a smaller area than the entire area of the base substrate 110, and only the driving chip 122 excluding the temperature sensor 130 and the NFC antenna 140 may be mounted on one surface of the circuit board 121.

For example, as shown in FIGS. 3 to 6, the base substrate 110 may include a plate-shaped first portion 111 having a predetermined area and a second portion extending from the first portion 111 to a predetermined length, and the second portion 112 may be a bar shape having a smaller area than the first portion 111, and the circuit board 121 may be disposed on one surface of the first portion 111.

In this case, the circuit board 121 may be disposed on one surface of the first portion 111 to be located at a position corresponding to a narrow area corresponding to a partial area of the entire area of the first portion 111, and the NFC antenna 140 may be disposed on one surface of the first portion 111 so as to surround an edge of the circuit board 121 from the outside of the circuit board 121 in the first portion 111.

That is, the circuit board 121 may be disposed on one surface of the first portion 111 so as to be located in an inner region of the NFC antenna 140, and the entire area of the circuit board 121 may be an area corresponding to a partial area of the total area corresponding to the inner region of the NFC antenna 140.

In addition, the NFC antenna 140 may be disposed on the first portion 111 to be electrically connected to the circuit board 121, and the temperature sensor 130 may be disposed on the second portion 112 so as to be located on the second portion 112, and may be electrically connected to the circuit board 121.

In this case, the NFC antenna 140 may be composed of a coil in which a wire having a predetermined length is wound a plurality of times, and the temperature sensor 130 may be electrically connected to the circuit board 121 through at least one wire 132 having one end connected to the circuit board 121.

Here, both ends of the NFC antenna 140 may be electrically connected to the circuit board 121 through soldering or the like.

Accordingly, in the disposable electronic thermometer 100 or 200 according to one embodiment of the present invention, there is no need to pattern the NFC antenna 140 or mount the temperature sensor 130 on the circuit board 121, and even if only the driving chip 122 is mounted on the circuit board 121, the circuit configuration for measuring the user's body temperature may be completed.

That is, in the disposable electronic thermometer 100 or 200 according to one embodiment of the present invention, even if the circuit board 121 has a small area in which the driving chip 122 may be mounted, the circuit configuration for measuring the user's body temperature may be completed, and therefore, the circuit board 121 may not require an additional area for forming the antenna pattern operating as the NFC antenna 140 or an additional area for mounting the temperature sensor 130 thereon.

As a result, in the present invention, the circuit board 121 may be formed to have a narrow area capable of covering an area of the driving chip 122 among the total area of the first portion 111 of the base substrate 110, instead of a large area capable of covering all of the driving chip 122, the NFC antenna 140 and the temperature sensor 130, and thus, the total amount of the circuit board used may be reduced, thereby lowering the production cost.

In addition, in the disposable electronic thermometer 100 or 200 according to one embodiment of the present invention, since the circuit board 121 may be locally disposed only on a partial area corresponding to the driving chip 122 among the total area of the base substrate 110, the flexibility of the base substrate 110 may be improved.

The temperature sensor 130 may measure the user's body temperature through driving of the control part 120 when power is supplied.

As described above, the temperature sensor 130 may be disposed on one surface of the base substrate 110 and may be electrically connected to the circuit board 121.

That is, the temperature sensor 130 may be disposed to be positioned on the second portion 112 of the base substrate 110, and may be connected to the circuit board 121 through at least one wire 132.

For example, the temperature sensor 130 may be disposed to be positioned at an end of the second portion 112 extending from the first portion 111 in a bar shape, and may be electrically connected to the circuit board 121 disposed on the first portion 111 via at least one wire 132.

Therefore, the temperature sensor 130 may be spaced apart from the circuit board 121 by a predetermined distance.

Accordingly, when the disposable electronic thermometer 100 or 200 according to one embodiment of the present invention is attached to the user's body by the adhesive layer 113, the temperature sensor 130 for measuring the body temperature may be stably attached to the user's body even though pressing only the local area where the temperature sensor 130 is disposed in the second portion 112 of the base substrate 110.

Figure 8:
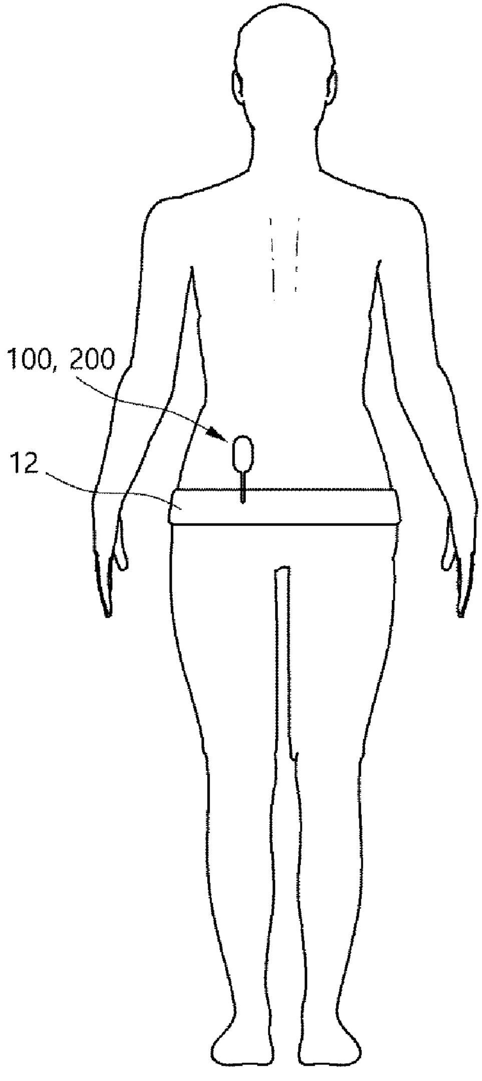
FIG. 8 is a view showing a state of use of a disposable electronic thermometer according to the present invention.

For example, as shown in FIG. 8, in a case in which the disposable electronic thermometer 100 or 200 according to one embodiment of the present invention is attached to the waist belt portion 12 of the user's body, the portion corresponding to the temperature sensor 130 may be stably attached to the user's body even if disposing only a part of the second portion 112 where the temperature sensor 130 is disposed at a position corresponding to the waist belt.

Accordingly, when using the disposable electronic thermometer 100 or 200 according to one embodiment of the present invention, since the temperature sensor 130 for measuring the body temperature may maintain a stable attached state to the user's body, the user's body temperature may be accurately measured. Further, since a part that is pressed through the waist belt is a small area, discomfort that the user may feel when moving may be minimized.

However, the attachment position of the disposable electronic thermometer 100 or 200 according to one embodiment of the present invention is not limited thereto, and the thermometer may be attached to various parts of the body where the user's body temperature may be measured, such as an armpit, a back, a side, a stomach, and the like.

In this case, the temperature sensor 130 may measure the user's body temperature in real time once according to the user's operation, or may periodically measure the user's body temperature at regular time intervals regardless of the user's operation.

Here, the user's body temperature information measured by the temperature sensor 130 may be stored in the memory part 123. A detailed description thereof will be provided later.

Accordingly, in the disposable electronic thermometer 100 or 200 according to one embodiment of the present invention, the body temperature information measured by the temperature sensor 130 while being attached to the user's skin may be stored in the memory part 123, whereby changes in the user's body temperature over time may be accumulated in the memory part 123.

Accordingly, the user may easily check a change trend of the body temperature through the result values of the body temperature stored in the memory part 123. That is, the user may easily check the amount of temperature change $\Delta t$ between two time points at which the body temperature is measured through the result values stored in the memory part 123.

The NFC antenna 140 may transmit the body temperature information measured by the temperature sensor 130 to an external electronic device in a wireless manner.

That is, the NFC antenna 140 may serve as a radiator for transmitting the body temperature information acquired by the temperature sensor 130 to the outside using a short-range wireless communication method.

Here, the external electronic device may be an electronic device having a built-in wireless communication module corresponding to the NFC antenna 140. For example, the external electronic device may be a portable terminal such as a smart phone.

Accordingly, the user may conveniently check the body temperature information measured by the temperature sensor 130 using the external electronic device.

In addition, when the body temperature information measured by the temperature sensor 130 is stored in the memory part 123, the NFC antenna 140 may transmit the data stored in the memory part 123 to the external electronic device.

As a specific example, the user may easily check the body temperature information transmitted to the portable terminal through the NFC antenna 140 when NFC tagging is performed.

Here, the body temperature information transmitted to the portable terminal may be the body temperature information measured in real time by the temperature sensor 130 or the body temperature information stored in the memory part 123. In addition, the body temperature information transmitted to the portable terminal may be both the body temperature information measured in real time by the temperature sensor 130 and the body temperature information stored in the memory.

Accordingly, the user may easily check the body temperature information measured in real time by the temperature sensor 130 or the body temperature information stored in the memory part 123, thereby easily checking the change trend of the body temperature.

That is, when the body temperature information stored in the memory part 123 is transmitted to the portable terminal through the NFC antenna 140, the user may easily check the amount of temperature change Δt between two time points at which the body temperature is measured from the body temperature information stored in the memory part 123, thereby easily checking the change trend of the body temperature through the body temperature information stored in the memory part 123.

Such an NFC antenna 140 may be a coil in which a wire having a predetermined length is wound a plurality of times as described above, and may be disposed on the first portion 111 to surround the edge of the circuit board 121 from the outside of the circuit board 121 while being electrically connected to the circuit board 121.

In this case, data transmitted to the portable terminal through the NFC antenna 140 during NFC tagging may be displayed through an app stored in the portable terminal. In addition, the data transmitted to the portable terminal through the NFC antenna 140 may be stored in the app itself.

Accordingly, the user may also check the change trend of the body temperature by using the data stored in the app as well as the data stored in the memory part 123.

In this case, as described above, the temperature sensor 130 may measure the user's body temperature in real time once according to the user's operation by using driving power supplied from the outside, or may periodically measure the user's body temperature at regular time intervals regardless of the user's operation by using the power of the built-in power supply part 170 as driving power.

Figure 4:
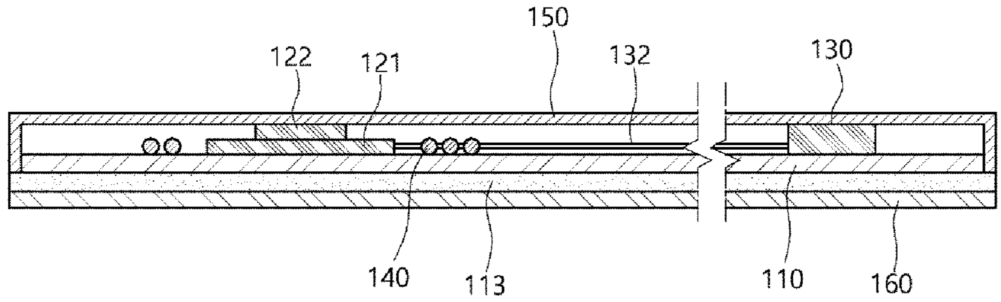
FIG. 4 is a cross-sectional view taken along line A-A of FIG. 3.

For example, as shown in FIGS. 3 and 4, the disposable electronic thermometer 100 according to one embodiment of the present invention does not have a built-in separate power supply part such as a battery, and may receive driving power from the outside only when the body temperature is measured.

That is, the control part 120 may be driven using the driving power supplied from the outside when the body temperature is measured. In this case, since the disposable electronic thermometer 100 according to the present embodiment does not require a separate battery, the production cost may be further reduced.

As a specific example, the control part 120 may receive the driving power through the NFC antenna 140 in an energy harvesting method during NFC tagging using an external electronic device such as a portable terminal.

That is, when a user intends to measure the body temperature by using the disposable electronic thermometer 100 attached to the body part, the user may NFC tag an external electronic device such as a portable terminal to the disposable electronic thermometer 100.

In this case, the control part 120 may receive the driving power through the NFC antenna 140 when the NFC tagging is performed, and the temperature sensor 130 may be driven through the control part 120 to measure the body temperature in real time.

In addition, the body temperature information measured in real time by the temperature sensor 130 may be transmitted to an external electronic device such as the portable terminal through the NFC antenna 140, and may also be stored in the memory part 123 of the control part 120.

Accordingly, the user may check the body temperature information measured in real time by using an app of an external electronic device such as the portable terminal.

Figure 5:
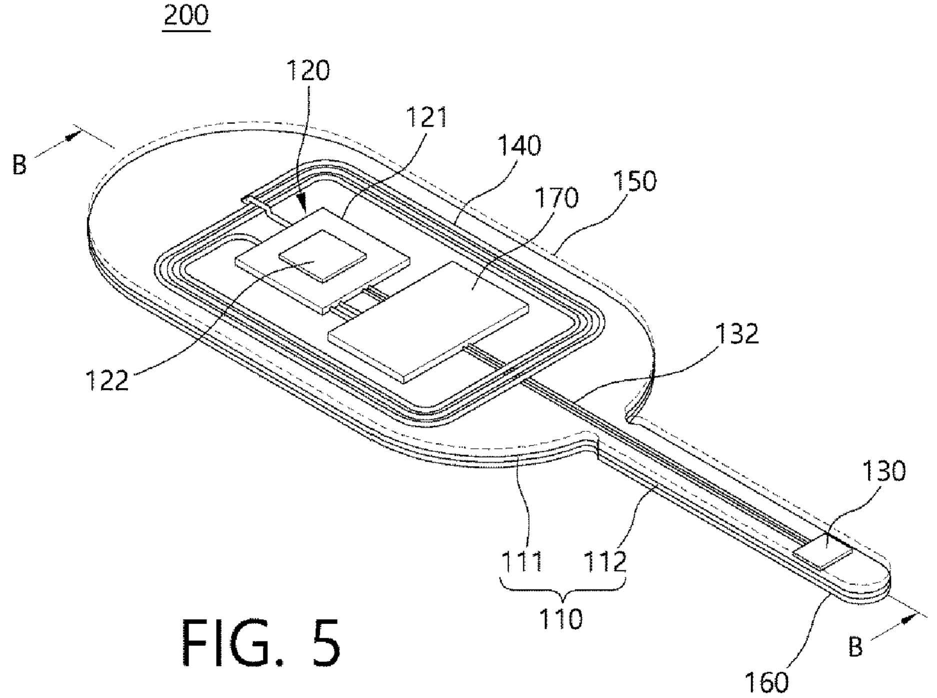
FIG. 5 is a view showing an internal configuration of a disposable electronic thermometer according to another embodiment of the present invention.
Figure 6:
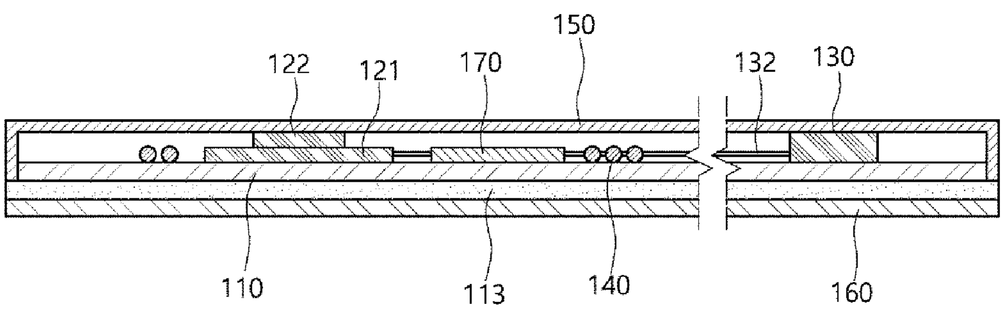
FIG. 6 is a cross-sectional view taken along line B-B of FIG. 5.

As another example, as shown in FIGS. 5 and 6, the disposable electronic thermometer 200 according to one embodiment of the present invention may include a built-in separate power supply part 170 such as a battery.

Such a power supply part 170 may be electrically connected to the circuit board 121, and may be disposed to be positioned on one surface of the base substrate 110.

Here, the power supply part 170 may be a coin battery or a prismatic battery known in the art, but may be a plate-shaped flexible battery so as to increase capacity while reducing overall weight and volume. As a non-limiting example, the power supply part 170 may be a paper battery or a printed battery known in the art.

That is, since the power supply part 170 of the disposable electronic thermometer 200 according to the present embodiment is composed of a plate-shaped flexible battery, the disposable electronic thermometer 200 may have a reduced overall weight and be implemented in a thin form while securing a sufficient driving power capacity.

In this case, the control part 120 may receive the driving power from the power supply part 170, and may measure the wearer's body temperature at regular time intervals by the temperature sensor 130.

That is, the disposable electronic thermometer 200 according to the present embodiment may periodically measure the user's body temperature by using the power from the power supply part 170 while being attached to the user's body part.

In addition, the body temperature information periodically measured by the temperature sensor 130 may be stored in the memory part 123, and the body temperature information stored in the memory part 123 may be transmitted to an external electronic device through the NFC antenna 140 during NFC tagging using the external electronic device such as a portable terminal.

Thus, the disposable electronic thermometer 200 according to the present embodiment may function as a data logger that periodically measures and stores the user's body temperature.

Accordingly, the user may easily check the body temperature information transmitted from the memory part 123 to the external electronic device such as the portable terminal through the NFC antenna 140 during the NFC tagging using an app.

The cover member 150 may be attached to one surface of the base substrate 110 to prevent the circuit board 121, the temperature sensor 130 and the NFC antenna 140 disposed on one surface of the base substrate 110 from being exposed to the outside.

Such a cover member 150 may be made of a material having flexibility.

Accordingly, even if the disposable electronic thermometer 100 or 200 according to one embodiment of the present invention is attached to a curved body part, since the disposable electronic thermometer 100 or 200 may be flexibly adapted to the body curves of the user, the disposable electronic thermometer 100 or 200 may be in close contact with the user's body.

For example, the cover member 150 may be a plate-shaped sheet formed of a fluoropolymer resin such as PET, PP or PE, or a release paper.

In this case, the cover member 150 may have heat insulation properties to block heat transfer from the outside to the temperature sensor 130 while having flexibility.

For example, the cover member 150 may be a plate-shaped film member, and the film member may be made of a material having flexibility and heat insulating properties.

Accordingly, even if an external temperature change occurs in a state in which the disposable electronic thermometer 100 or 200 according to one embodiment of the present invention is attached to the user's body, external heat may be prevented from being transferred to the temperature sensor 130 through the cover member 150.

As a result, the body temperature information measured by the temperature sensor 130 may be more accurate.

However, the material of the cover member 150 is not limited thereto. Further, the cover member 150 may include a separate heat insulating layer (not shown) provided on at least one surface thereof. In this case, the cover member 150 may be made of a material having heat insulation or a material without heat insulation.

Although one embodiment of the present invention have been described above, the spirit of the present invention is not limited to the embodiment presented in the subject specification; and those skilled in the art who understands the spirit of the present invention will be able to easily suggest other embodiments through addition, changes, elimination, and the like of elements without departing from the scope of the same spirit, and such other embodiments will also fall within the scope of the present invention.

The invention claimed is:

1. A disposable electronic thermometer comprising:

a base substrate including an adhesive layer formed on one surface, the adhesive layer configured to be attached to a user's body;

a controller including a circuit board disposed on one surface of the base substrate and at least one driving chip mounted on the circuit board;

a temperature sensor disposed on one surface of the base substrate and electrically connected to the circuit board, the temperature sensor configured to measure the user's body temperature;

a Near Field Communication (NFC) antenna electrically connected to the circuit board and disposed on one surface of the base substrate; and a cover member attached to one surface of the base substrate to prevent external exposure of the circuit board, the temperature sensor and the NFC antenna, wherein the base substrate includes a plate-shaped first portion in which the circuit board and the NFC antenna are disposed, and a second portion formed in a bar shape and extending lengthwise from the first portion, the second portion having a smaller area than the first portion and having the temperature sensor disposed on the second portion, wherein the NFC antenna is a separate wire-wound coil member disposed on the one surface of the base substrate, is configured as a coil in which a wire having a predetermined length is wound multiple times, and is disposed on the first portion to surround an outside of the circuit board, wherein the NFC antenna is not an antenna pattern formed on the circuit board, and both ends of the NFC antenna are electrically connected to the circuit board, wherein among the at least one driving chip, the NFC antenna, and the temperature sensor, only the at least one driving chip is mounted on the circuit board, and neither the NFC antenna nor the temperature sensor is mounted on the circuit board, and the circuit board is disposed in an inner region of the NFC antenna without an antenna pattern formed thereon so as to occupy only a partial area of the first portion, and wherein the temperature sensor is disposed at an end portion of the second portion and is electrically connected to the circuit board through at least one wire extending from the circuit board to the second portion, wherein the at least one wire extends along the second portion to the temperature sensor, and the temperature sensor is not mounted on the circuit board.

2. The disposable electronic thermometer according to claim 1, wherein the base substrate is a porous substrate.

3. The disposable electronic thermometer according to claim 1, wherein the cover member is a plate-shaped film member.

4. The disposable electronic thermometer according to claim 1, wherein the disposable electronic thermometer receives driving power through the NFC antenna when NFC tagging is performed.

5. The disposable electronic thermometer according to claim 4, wherein the controller further includes a memory for storing body temperature information measured by the temperature sensor.

6. The disposable electronic thermometer according to claim 4, wherein the controller transmits body temperature information measured by the temperature sensor to the outside of the circuit board through the NFC antenna.

7. The disposable electronic thermometer according to claim 1, wherein the disposable electronic thermometer further includes a power supply for providing driving power to the controller.

8. The disposable electronic thermometer according to claim 7, wherein the controller further includes a memory for storing body temperature information measured by the temperature sensor;

wherein the controller is configured to measure the user's body temperature at regular time intervals through the temperature sensor and store the measured temperature information in the memory, and wherein the measured temperature information stored in the memory is transmitted to the outside through the NFC antenna when NFC tagging is performed.

* * * * *